(12) United States Patent
Haase et al.

(10) Patent No.: US 9,410,882 B2
(45) Date of Patent: Aug. 9, 2016

(54) TURBIDIMETER

(71) Applicant: HACH LANGE GMBH, Berlin (DE)

(72) Inventors: Barbara Haase, Berlin (DE); Manfred Battefeld, Duesseldorf (DE); Andreas Mitreiter, Kleinmachnow (DE); Michael Kussmann, Duesseldorf (DE); Bas De Heij, Dormagen (DE); Clemens Hanschke, Berlin (DE); Wayne Perdue, Berlin (DE)

(73) Assignee: HACH LANGE GMBH, Berlin (DE)

( * ) Notice: Subject to any disclaimer, the term of this patent is extended or adjusted under 35 U.S.C. 154(b) by 0 days.

(21) Appl. No.: 14/890,428

(22) PCT Filed: May 13, 2013

(86) PCT No.: PCT/EP2013/059846
§ 371 (c)(1),
(2) Date: Nov. 11, 2015

(87) PCT Pub. No.: WO2014/183778
PCT Pub. Date: Nov. 20, 2014

(65) Prior Publication Data
US 2016/0109365 A1    Apr. 21, 2016

(51) Int. Cl.
*G01N 21/00* (2006.01)
*G01N 21/51* (2006.01)

(52) U.S. Cl.
CPC .......... *G01N 21/51* (2013.01); *G01N 2021/513* (2013.01); *G01N 2201/0636* (2013.01)

(58) Field of Classification Search
CPC ............................... G01N 21/00; G01N 21/51
USPC ......................................................... 356/338
See application file for complete search history.

(56) References Cited

U.S. PATENT DOCUMENTS

| 4,129,383 | A | * | 12/1978 | Malinowski | ......... | G08B 17/107 250/574 |
| 4,690,560 | A | * | 9/1987 | Coogan | .................. | G01N 21/51 356/236 |
| 6,705,736 | B1 | * | 3/2004 | Pressler | ................. | G02B 5/001 359/853 |
| 7,362,517 | B2 | * | 4/2008 | Togino | .................. | G02B 13/06 348/36 |
| 8,687,286 | B2 | * | 4/2014 | Palumbo | ................ | G02B 5/001 359/709 |
| 2006/0103842 | A1 | * | 5/2006 | Tokhtuev | ............... | G01N 21/53 356/338 |
| 2012/0170137 | A1 | | 7/2012 | Palumbo | | |

(Continued)

FOREIGN PATENT DOCUMENTS

| DE | 934 978 C | 11/1955 |
| EP | 1 826 556 A2 | 8/2007 |
| GB | 1 298 658 A | 12/1972 |

*Primary Examiner* — Roy M Punnoose
(74) *Attorney, Agent, or Firm* — Norman B. Thot

(57) ABSTRACT

A turbidimeter for measuring a turbidity of a liquid sample in a sample cuvette includes a cuvette receiving device configured to position the sample cuvette in a defined cuvette position, a light source configured to generate a parallel light beam in the sample cuvette, an annular 45° collecting mirror configured to surround the sample cuvette, a scattering body arranged concentric to the annular 45° collecting mirror, a scattering light detector arranged to receive light scattered by the scattering body, and an annular 45° concentration mirror arranged coaxially to the annular 45° collecting mirror and optically opposite to the annular 45° collecting mirror. The annular 45° collecting mirror is arranged concentric to the light beam. The annular 45° concentration mirror is configured to surround the scattering body.

10 Claims, 2 Drawing Sheets

(56) References Cited

U.S. PATENT DOCUMENTS

2013/0135613 A1* 5/2013 Palumbo ............... G01N 21/01 356/244

2014/0049836 A1* 2/2014 Palumbo ............... G01N 21/01 359/709

* cited by examiner

TURBIDIMETER

CROSS REFERENCE TO PRIOR APPLICATIONS

This application is a U.S. National Phase application under 35 U.S.C. §371 of International Application No. PCT/EP2013/059846, filed on May 13, 2013. The International Application was published in English on Nov. 20, 2014 as WO 2014/183778 A1 under PCT Article 21(2).

FIELD

The present invention relates to a turbidimeter for measuring the turbidity of a liquid sample.

BACKGROUND

A conventional turbidimeter determines the concentration of solid particles suspended in a liquid sample by projecting a light beam through a cuvette comprising the liquid sample. A light detector detects the amount of light scattered by the suspended solid particulates in a right angle to the light beam axis. If the light detector detects light scattered in one single sector of the circumference, the signal of the light detector is relatively low.

US 2012/0170137 A1 describes different circular mirror and prism arrangements which coaxially surround the liquid sample cuvette to direct radially scattered light over the complete circumference to the light detector. These arrangements can lead to a significantly increased signal/noise ratio. These arrangements are, however, generally very sensitive to geometrical inaccuracies of the complete optical arrangement in addition to being very sensitive to local inhomogeneities of the turbidity of the liquid sample in the cuvette.

SUMMARY

An aspect of the present invention is to increase the general accuracy of a turbidimeter measuring and determining the turbidity of a liquid sample.

In an embodiment, the present invention provides a turbidimeter for measuring a turbidity of a liquid sample in a sample cuvette which includes a cuvette receiving device configured to position the sample cuvette in a defined cuvette position, a light source configured to generate a parallel light beam in the sample cuvette, an annular 45° collecting mirror configured to surround the sample cuvette, a scattering body arranged concentric to the annular 45° collecting mirror, a scattering light detector arranged to receive light scattered by the scattering body, and an annular 45° concentration mirror arranged coaxially to the annular 45° collecting mirror and optically opposite to the annular 45° collecting mirror. The annular 45° collecting mirror is arranged concentric to the light beam. The annular 45° concentration mirror is configured to surround the scattering body.

BRIEF DESCRIPTION OF THE DRAWINGS

The present invention is described in greater detail below on the basis of embodiments and of the drawings in which.

DETAILED DESCRIPTION

Figure 1:
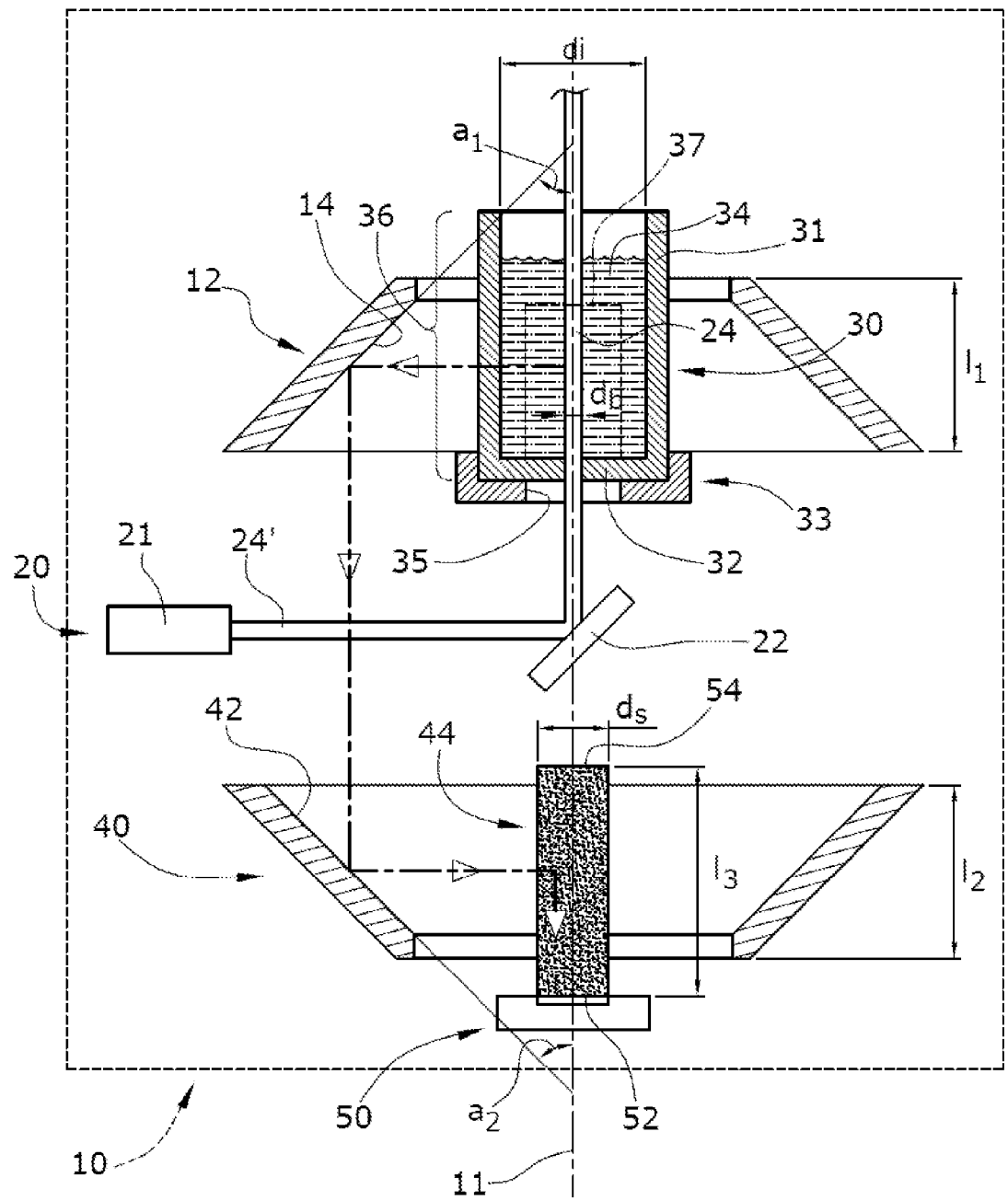
FIG. 1 shows the optics of a turbidimeter in a longitudinal cross-section.
Figure 2:
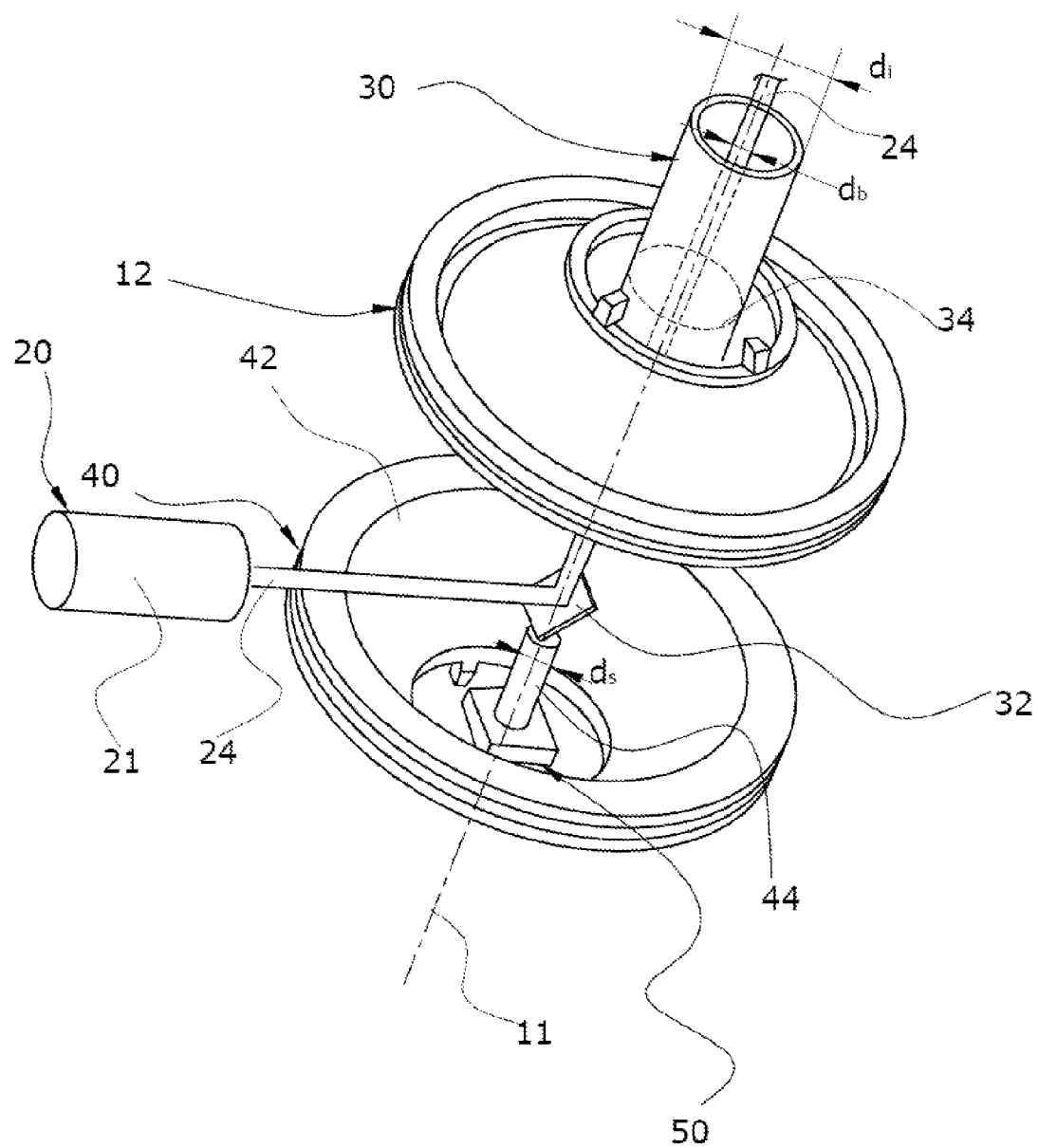
FIG. 2 shows the optics of the turbidimeter of FIG. 1 in a perspective view.

The turbidimeter according to the present invention is provided with a cuvette receiving device for positioning the sample cuvette in a defined cuvette position. The turbidimeter can generally be designed for a continuous determination of the turbidity so that the cuvette is fixed in a defined cuvette position and the liquid sample flows through the cuvette. The turbidimeter can alternatively be designed for use with exchangeable cuvettes which are already filled with the liquid sample when inserted into the turbidimeter. The cuvette receiving device provides that the cuvette is more or less exactly positioned in a defined cuvette position and that the transparent cuvette wall portion through which the light beam enters the cuvette is positioned in a defined angle, for example, in a rectangular angle with respect to the light beam axis.

A light source generates a light beam which is directed into the cuvette. The light beam itself is parallel, and can, for example, be a monochromatic laser beam generated by a laser diode. The diameter of the laser beam inside the cuvette should not be too small, and can, for example, have a diameter of a few millimeters, such as, for example, of 3 mm.

A collecting mirror is arranged to surround the cuvette and is designed as an annular 45° collecting mirror arranged concentric with the light beam axis in the cuvette. The collecting mirror does not necessarily completely surround the cuvette, but can, for example, be arranged to completely surround the cuvette by 360°. The collecting mirror axially reflects the scattered light coming more or less radially from the liquid sample, and, more precisely, coming from the solid particles reflecting the light of the light beam penetrating the liquid sample inside the cuvette. The collecting mirror is not necessarily defined by a single-surface mirror, but can alternatively be defined by a mirror body with two or more mirror surfaces so that the mirror body is, for example, defined by a penta prism.

A separate concentration mirror is arranged coaxially and optically opposite to the collecting mirror. The concentration mirror is also designed as an annular 45° mirror so that the more or less axial light current from the collecting mirror is reflected by the concentration mirror radially inside to the optical axis defined by the light beam and the collecting mirror. The light current between the collecting mirror and the concentration mirror defines a cylindrical ring. The concentration mirror is not necessarily completely closed in circumferential direction, but can, for example, be completely closed. Both mirrors can, for example, define conical and ring-like closed mirror surfaces. The concentration mirror can, analogously to the collecting mirror, be defined by a mirror body with two or more mirror surfaces.

The concentration mirror surrounds a scattering body which is solid. The scattering body is arranged concentric to the collecting mirror in the transversal plane defined by the collecting mirror. The scattering body is translucent, but is thereby neither completely transparent nor completely impervious for the light of the light source. The scattering characteristic of the scattering body can, for example, be homogeneous over the entire volume of the scattering body. The light reflected by the collecting mirror radially inwardly penetrates the scattering body so that this light is diffused and scattered in all directions by the scattering body. The scattering body can, for example, be cylindrical over its entire length. The scattering body can, for example, consist of a type of opal glass or of a plastic substance homogenously filled with scattering particles which can, for example, be micro-particles. The plastic substance can be PMMA or another highly transparent substance. The particles can, for example, be calcium phosphate, fluorides, stannic oxide, titanium oxide, or other suitable particle powders. The particle size should be in the range of the wavelength of the light generated by the light source and/or in the range of the sensitivity wavelength of the light detector, for example, in the range of 1.0 to 5.0 μm.

A scattering light sensor is arranged and is provided to receive a fraction of the light scattered by the scattering body which is scattered axially in the direction of the light sensor. The light sensor can, for example, be directly attached to the scattering body to reduce transmission losses to a minimum. The scattering light sensor is arranged at one axial end of the scattering body. The scattering light sensor can, for example, be sensible for the wavelength range of the light generated by the light source. The scattering light sensor can be provided with an optic element which directs the light of the complete surface of the plane axial end surface of the scattering body to the sensor element which might be much smaller than the end surface. The light sensor element can be a photoelectric element such as a photodiode.

In an embodiment of the present invention, relatively simple and inexpensive optics can be obtained by providing two annular 45° mirrors opposite to each other which are configured to direct the light scattered from the liquid sample in a 90° angle and by providing a turbid scattering body. The geometry of the 45° collecting mirror and the opposite 45° concentration mirror has the effect that scattered sample light not coming directly from the center axis of the collecting mirror still hits the scattering body so that scattered sample light which does not come directly from the center axis of the collecting mirror is also detected by the light detector. The sample liquid volume examined in the cuvette can therefore be significantly increased. Local turbidity inhomogeneities do not, therefore, affect the accuracy of the measurement result to any great extent.

In an embodiment of the present invention, the diameter of the scattering body can, for example, be greater than the light beam diameter in the cuvette, and can, for example, be smaller than the inner diameter of the cylindrical cuvette. The geometry and volume of the scattering body is more or less exactly identical with the geometry of the monitoring volume inside the cuvette which is monitored by the light detector, i.e., all light scattered from inside the monitoring volume inside the cuvette is received by the scattering body. Since the diameter of the scattering body is greater than the light beam diameter, deviations of the light beam caused by a not perfectly-formed cuvette bottom wall need not affect the amount of the light transmitted to the scattering body and received by the light detector. The turbidimeter therefore becomes more tolerant with respect to the optical arrangement which directs the light beam into the cuvette so that greater tolerances are acceptable for the turbidimeter's optics and for the cuvette. Light scattered by the cuvette body is not projected into the scattering body since the diameter of the scattering body is smaller than the inner diameter of the cylindrical cuvette. The diameter of the scattering body can, for example, be significantly smaller than the inner diameter of the cuvette so that the monitored volume does not interfere with the cuvette body even if the cuvette is not positioned exactly axially with respect to the light beam.

In an embodiment of the present invention, the diameter of the scattering body can, for example, be at least 2.0 times, for example, at least 3.0 times the light beam diameter. This dimensioning of the diameter of the scattering body allows deviations of the light beam inside the cuvette of a few degrees without resulting in a significant change of the scattered light quantity detected by the light detector.

In an embodiment of the present invention, the axial length of the two mirrors can, for example, be identical. The axial length of the scattering body can, for example, be identical with the axial length of the two mirrors. This configuration provides a uniform monitoring volume which is not significantly influenced by inaccuracies of the light beam optics or of the cuvette.

In an embodiment of the present invention, a light beam mirror can, for example, be arranged axially between the collecting mirror and the concentration mirror. The light beam mirror reflects the light coming from the light source axially into the cuvette. In other words, the light beam mirror couples-in the light coming from the light source into the longitudinal axis defined by the collecting mirror, the concentration mirror, and the scattering body. The light beam mirror can, for example, be arranged with a mirror angle of 45° with respect to the longitudinal axis so that the light beam coming radially from the light source is reflected by a 90° with respect to the longitudinal axis.

By coupling-in the light beam between the concentration mirror and the collecting mirror, the apparatus can remain open at the top so that the cuvette can be exchanged from the apparatus' top without interfering with any of the light beam optics.

The drawings show a turbidimeter 10 for measuring and determining the turbidity of a liquid sample 34 in a sample cuvette 30. In the present embodiment, the turbidimeter 10 is not a so-called process device, but is a so-called laboratory device which is not necessarily used only in a laboratory, but which can be used to determine the turbidity of a single isolated liquid sample 34 in a cuvette. The laboratory device is not suitable for a continuous determination of a sample flow.

The turbidity of a liquid is an indication of the concentration of solid particles suspended in the liquid sample 34. The turbidity is determined by projecting a light beam into the liquid sample and by measuring the light intensity of the light scattered by the liquid sample 34 at an angle of 90° to the light beam's longitudinal axis in the liquid sample 34.

The turbidimeter 10 is provided with a housing (not shown) with an opening for inserting and ejecting the sample cuvette 30 into and from a cuvette receiving device 33 inside the housing. The cuvette receiving device 33 positions the inserted sample cuvette 30 in a defined cuvette position 36 with a tilting angle precision of a few degrees. The cuvette receiving device 33 is circular in form and is provided with a center opening 35 which allows a longitudinal axial light beam 24 to axially pass the cuvette receiving device 33 and to run through a cuvette bottom wall 32 into the cuvette interior comprising the liquid sample 34. The sample cuvette 30 is primarily defined by a transparent and cylindrical cuvette body 31 comprising the cuvette bottom wall 32 which is plane.

The inserted sample cuvette 30 is surrounded by a coaxial collecting mirror 12 which is ring-like in shape and which is provided with a center opening at its tight axial end through which a top end of the sample cuvette 30 projects. A mirror surface 14 of the coaxial collecting mirror 12 is exactly defined by a conus with a conus angle $a_1$ of 45°.

A concentration mirror 40 is provided coaxially with and opposed to the coaxial collecting mirror 12. A mirror surface 42 of the concentration mirror 40 is identical in shape and size with the mirror surface 14 of the coaxial collecting mirror 12. A cone angle $a_2$ of the mirror surface 42 of the concentration mirror 40 is consequently exactly −45° with respect to a central longitudinal axis 11. The concentration mirror 40 is positioned in a position exactly opposite to that of coaxial collecting mirror 12 so that light scattered radially by the liquid sample 34 is reflected by the coaxial collecting mirror 12 into an exactly axial direction and is reflected by the concentration mirror 40 back to the center into an exactly radial direction.

A solid scattering body 44 is provided and positioned exactly in the center and in the plane of the concentration mirror 40. The solid scattering body 44 is cylindrical in shape, is made of plastic, and is provided so as to be homogenously translucent in its entire volume. In other words, the solid scattering body 44 is not clear but consists of a transparent solid plastic body with micro-particles uniformly distributed in the volume of the solid scattering body 44. The microparticles scatter the light entering the solid scattering body 44 from radial directions into all directions so that the entering light is diffused. As a consequence, a fraction of the entering light is scattered in both axial directions. The solid scattering body 44 can be made of transparent PMMA with micro particles of titanium oxide of a particle size of 1 to 2 μm. Both the distal scattering body end 52 and the axially proximal end 54 of solid scattering body 44 are planar. The axially proximal end 54 of the solid scattering body 44 can be provided with a plane reflecting surface redirecting the scattered light to the distal scattering body end 52.

A light source 20 is arranged in a plane axially between the concentration mirror 40 and the coaxial collecting mirror 12. The light source 20 can be a laser diode 21 generating a parallel light beam 24' of a diameter $d_b$ of, for example, 3.0 mm. The parallel light beam 24' emitted by the light source 20 lies in a transversal plane rectangular to the central longitudinal axis 11 and is reflected by a plane light beam mirror 22 into an axial direction coaxial with the central longitudinal axis 11. The plane light beam mirror 22 is arranged in an angle of 45° with respect to the central longitudinal axis 11. The reflected longitudinal axial light beam 24 proceeds through the center opening 35 and the cuvette bottom wall 32 into the liquid sample 34.

A light detector 50 is provided at the distal scattering body end 52 of the solid scattering body 44. The light detector 50 is sensitive for the light emitted by the light source 20. The light detector 50 detects the light which is scattered and reflected inside the solid scattering body 44 in the distal axial direction. The light detector 50 can, for example, be sensitive over the entire diameter of a surface of the distal scattering body end 52 of the solid scattering body 44.

As an alternative to a reflective surface at the axially proximal end 54 of the solid scattering body 44, a second light detector (not shown) can be provided at the axially proximal end 54 of the solid scattering body 44.

The axial lengths $l_1, l_2, l_3$ of the collecting mirror 12, the concentration mirror 40, and the solid scattering body 44, are more or less identical. The diameter $d_s$ of the cylindrical solid scattering body 44 is about 3.0 times the diameter $d_b$ of the parallel light beam 24' in the sample cuvette 30.

The shape and volume of the solid scattering body 44 is identical to the projection thereof caused by the concentration mirror 40 and the coaxial collecting mirror 12 in the interior of the sample cuvette 30 so that a corresponding monitoring volume 37 is defined inside the sample cuvette 30. The corresponding monitoring volume 37 has the same diameter $d_s$ and axial length $l_3$ as the solid scattering body 44 and defines the volume which is monitored by the light detector 50. The corresponding monitoring volume 37 is larger in diameter than the parallel light beam 24 so that the optical arrangement is tolerant with respect to the exact position of the parallel light beam 24 inside the liquid sample 34. The outer diameter $d_s$ of the solid scattering body 44 is, however, significantly less than the inner diameter $d_i$ of the sample cuvette 30.

The present invention is not limited to embodiments described herein; reference should be had to the appended claims.

What is claimed is:

1. A turbidimeter for measuring a turbidity of a liquid sample in a sample cuvette, the turbidimeter comprising:
    a cuvette receiving device configured to position the sample cuvette in a defined cuvette position;
    a light source configured to generate a parallel light beam in the sample cuvette;
    an annular 45° collecting mirror configured to surround the sample cuvette, the annular 45° collecting mirror being arranged concentric to the light beam;
    a scattering body arranged concentric to the annular 45° collecting mirror;
    a scattering light detector arranged to receive light scattered by the scattering body; and
    an annular 45° concentration mirror arranged coaxially to the annular 45° collecting mirror and optically opposite to the annular 45° collecting mirror, the annular 45° concentration mirror being configured to surround the scattering body.

2. The turbidimeter as recited in claim 1, wherein the annular 45° collecting mirror and the annular 45° concentration mirror together define a conical and ring-like closed mirror surface.

3. The turbidimeter as recited in claim 1, wherein the annular 45° collecting mirror and the annular 45° concentration mirror each comprise a mirror surface which have an identical shape.

4. The turbidimeter as recited in claim 1, wherein the scattering body has a cylindrical shape.

5. The turbidimeter as recited in claim 1, wherein,
    the scattering body comprises a scattering body diameter,
    the sample cuvette comprises a sample cuvette light beam diameter and a cylindrical cuvette body which comprises a cylindrical cuvette body inner diameter,
    the scattering body diameter is larger than the sample cuvette light beam diameter, and
    the scattering body diameter is smaller than the cylindrical cuvette body inner diameter.

6. The turbidimeter as recited in claim 5, wherein the scattering body diameter is at least 2.0 times larger than the sample cuvette light beam diameter.

7. The turbidimeter as recited in claim 5, wherein the scattering body diameter is at least 3.0 times larger than the sample cuvette light beam diameter.

8. The turbidimeter as recited in claim 1, wherein,
    the annular 45° collecting mirror comprises an annular 45° collecting mirror axial length,
    the annular 45° concentration mirror comprises an annular 45° concentration mirror axial length, and
    the annular 45° collecting mirror axial length is identical to the annular 45° concentration mirror axial length.

9. The turbidimeter as recited in claim 8, wherein,
    the scattering body comprises a scattering body axial length, and
    the scattering body axial length is the same as each of the annular 45° collecting mirror axial length and the annular 45° concentration mirror axial length.

10. The turbidimeter as recited in claim 1, further comprising:
    a light beam mirror arranged axially between the annular 45° collecting mirror and the annular 45° concentration mirror, the light beam mirror being configured to reflect light from the light source axially into the sample cuvette.

* * * * *